(12) United States Patent
Weber et al.

(10) Patent No.: US 7,744,644 B2
(45) Date of Patent: Jun. 29, 2010

(54) MEDICAL ARTICLES HAVING REGIONS WITH POLYELECTROLYTE MULTILAYER COATINGS FOR REGULATING DRUG RELEASE

(75) Inventors: Jan Weber, Maple Grove, MN (US); Rachel Neuendorf, Berkeley, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 274 days.

(21) Appl. No.: 10/805,576

(22) Filed: Mar. 19, 2004

(65) Prior Publication Data

US 2005/0208100 A1 Sep. 22, 2005

(51) Int. Cl.
*A61F 2/06* (2006.01)
*A61F 2/02* (2006.01)

(52) U.S. Cl. .................... 623/1.42; 623/23.72
(58) Field of Classification Search ....... 623/1.15–1.22, 623/1.39–1.46
See application file for complete search history.

(56) References Cited

U.S. PATENT DOCUMENTS

| | | | | |
|---|---|---|---|---|
| 5,735,896 A | * | 4/1998 | Amon et al. | 424/423 |
| 5,837,377 A | * | 11/1998 | Sheu et al. | 428/412 |
| 6,120,535 A | * | 9/2000 | McDonald et al. | 623/1.39 |
| 6,240,616 B1 | * | 6/2001 | Yan | 29/527.2 |
| 6,245,579 B1 | * | 6/2001 | Wenz et al. | 436/530 |
| 6,254,632 B1 | | 7/2001 | Wu et al. | 623/1.15 |
| 6,306,422 B1 | * | 10/2001 | Batich et al. | 424/423 |
| 6,309,660 B1 | * | 10/2001 | Hsu et al. | 424/425 |
| 6,360,129 B1 | * | 3/2002 | Ley et al. | 607/127 |
| 6,399,528 B1 | | 6/2002 | Krell et al. | |
| 6,506,437 B1 | * | 1/2003 | Harish et al. | 427/2.25 |
| 6,530,951 B1 | * | 3/2003 | Bates et al. | 623/1.45 |

(Continued)

FOREIGN PATENT DOCUMENTS

WO WO 99/47252 9/1999

(Continued)

OTHER PUBLICATIONS

Rilling, P.; Pommersheim, Walter R.; Vogt, W. "Encapsulation of cytochrome C by multilayer microcapsules. A model for improved enzyme immobilization". Journal of Membrane Science vol. 129. 1997. pp. 283-287.

(Continued)

*Primary Examiner*—Alvin J Stewart
(74) *Attorney, Agent, or Firm*—Mayer & Williams PC; David B. Bonham; Keum J. Park (57) ABSTRACT

The medical articles which including the following: (a) a ceramic or metallic region whose surface includes a plurality of depressions, (b) a multilayer coating region including multiple polyelectrolyte layers deposited over the surface of the ceramic or metallic region; and (c) a therapeutic agent disposed beneath or within the multilayer coating region. According to another aspect of the present invention, medical articles are provided, which include: (a) a ceramic or metallic region, (b) a multilayer coating region including multiple polyelectrolyte layers deposited over a surface of the ceramic or metallic region, the multilayer coating region including a plurality of protuberances; and (c) a therapeutic agent disposed within regions beneath the protuberances. Also described herein are methods of making such medical articles, and methods of administering a therapeutic agent to a patent using such medical articles.

38 Claims, 6 Drawing Sheets

U.S. PATENT DOCUMENTS

| | | | |
|---|---|---|---|
| 6,558,733 B1 | 5/2003 | Hossainy et al. | 427/2.24 |
| 6,596,699 B2 | 7/2003 | Zamora et al. | |
| 6,660,034 B1 * | 12/2003 | Mandrusov et al. | 623/1.42 |
| 6,663,662 B2 * | 12/2003 | Pacetti et al. | 623/1.13 |
| 6,709,379 B1 * | 3/2004 | Brandau et al. | 600/3 |
| 6,712,845 B2 * | 3/2004 | Hossainy | 623/1.42 |
| 6,753,071 B1 * | 6/2004 | Pacetti | 428/212 |
| 6,849,089 B2 * | 2/2005 | Stoll | 623/1.42 |
| 6,940,580 B2 * | 9/2005 | Winterton et al. | 351/160 H |
| 7,163,555 B2 * | 1/2007 | Dinh | 623/1.42 |
| 7,179,289 B2 * | 2/2007 | Shanley | 623/1.42 |
| 2002/0037383 A1 | 3/2002 | Spillman | |
| 2002/0061326 A1 | 5/2002 | Li et al. | |
| 2003/0157260 A1 | 8/2003 | Rubner et al. | |
| 2003/0175517 A1 | 9/2003 | Voigt et al. | |
| 2003/0219909 A1 | 11/2003 | Lally et al. | |
| 2004/0249469 A1 | 12/2004 | Cohen et al. | 623/23.6 |
| 2005/0172852 A1 * | 8/2005 | Anderson et al. | 106/31.03 |

FOREIGN PATENT DOCUMENTS

| | | |
|---|---|---|
| WO | WO 02/32347 A2 | 4/2002 |
| WO | WO 03/035278 A1 | 5/2003 |
| WO | WO 2005/018501 A1 | 3/2005 |

OTHER PUBLICATIONS

Pommersheim, Rainer; Schrezenmeir, Jurgen; Vogt, Walter. "Immobilization of enzymes by multilayer microcapsules" Macromol. Chem. Phys. vol. 195. 1994. pp. 1557-1567.

Chung, A.J. and Rubner, M.F., Methods of Loading and Releasing Low Molecular Weight Cationic Molecules in Weak Polyelectrolyte Multilayer Films, Langmuir 2002, 18, 1176-1183.

Frank Caruso et al., Microencapsulation of Uncharged Low Molecular Weight Organic Materials by Polyelectrolyte Multilayer Self-assembly, *Langmuir* 2000, 16, 8932-8936.

Gi-Ra, Yi et al., Ordered Macroporous Particles by Colloidal Templating, *Chem. Mater.* 2001, 13, 2613-2618.

Singh, R.S., Grimes, C.A., Dickey, E.C. Fabrication of nanoporous TiO2 films through Bernard-Marangoni convection, *Materials Resources Innovations*, 2002, 5:178-184.

Chan, V.Z.-H et al. Ordered Bicontinuous Nanoporous and Nanorelief Ceramic Films from Self Assembling Polymer Precursors, *Science*, Nov. 26, 1999, v286, i5445, p. 1716-1719.

Shchukin, D.G. et al., Micron-Scale Hollow Polyelectrolyte Capsules with Nanosized Magnetic Fe3O4 Inside, Materials Letters 57, 1743-1747, 2003.

Radtchenko, I.L. et al., A Novel Method for Encapsulation of Poorly Water-soluble Drugs: Precipitation in Polyelectrolyte Multilayer Shells, International Journal of Pharmaceutics, 242, 219-223 (2002).

Radtchenko, I.L. et al, .Assembly of Alternated Multivalent Ion/Polyelectrolyte Layers on Colloidal Particles. Stability of the Multilayers and Encapsulation of Macromolecules into Polyelectrolyte Capsules, Journal of Colloid and Interface Science, 230, 272-280 (2000).

Whau, Winky L. et al., Surface-chemistry technology for microfluidics, *J. Micromech. Microeng.* 13 (2003) 272-278.

Radtchenko et al., Incorporation of macromolecules into polyelectrolyte micro and nanocapsules via surface controlled precipitation on colloidal particles, *Colloids and Surfaces A: Physicochemical and Engineering Aspects* 202 (2002) 127-133.

Moya, S. et al., Polyelectrolyte multilayer capsules templated on biological cells: core oxidation influences layer chemistry, *Colloids and Surfaces A: Physicochemical and Engineering Aspects* 183-185 (2001) 27-40.

Antipov, Alexei A. et al., Polyelectrolyte multilayer capsule permeability control, *Colloids and Surfaces A: Physicochemical and Engineering Aspects* 198-200 (2002) 535-541.

Qiu, Xingping et al.,Studies on the Drug Release Properites of Polysaccharide Multilayers Encapsulated Ibuprofen Microparticles, *Langmuir* 2001, 17, 5375-5380.

Antipov, Alexei A. et al., Sustained Release Properties of Polyelectrolyte Multilayer Capsules, *J. Phys. Chem. B* 2001, 105; 2281-2284, Oct. 27, 2000.

http://www.bmed.mcgill.ca/tabrizian/People_pages/Benjamin2.htm™cOMMUNICATIONS, Thierry, Benjamin, Development of new strategies for endovascular revascularization procedures, 1-7, date unknown but before the filing of this application.

http://people.ccmr.cornell.edu/~uli/Pages/meso-syn.html, Wiesner Research Group, Synthesis of Mesoporous Materials, 1-2, date unknown but before the filing of this application.

https://engineering.purdue.edu/BME/Seminars/2003/july_14_html, Graduate Seminar, Stent coating for drug delivery: Coating polymeric micelles using polyelectrolytes Purdue University Biomedical Engineering Seminar, 2003, 1-2, Jul. 14, 2003.

http://www.ccmr.cornell.edu/—uli/Pages/mesoporous.html, Wiesner Research Group, Mesoporous Materials Through Self-Esteem, 1-2, date unknown but before the filing of this application.

http://www.hmi.de/people/chemseddine/group.htm, 1-3, date unknown but before the filing of this application.

http://web.mit.edu/newsoffice/nr/1999/gyroid.htm, MIT researcher's intricate ceramic nanostructures have many potential uses, MIT News, 1-3, Nov. 25, 1999.

https://engineering.purdue.edu/ChE/Nano/NanoChmE/NSE_Topical_2001/SynthesisandCharacterizationofNovelNanoporousMaterials2.htm,2001, pp. 1-8.

Dinh, Nam et al., University of Santa Barbara, Magnetic Drug Targeting: A novel use of magnetic fields and magnetic particles to deliver therapeutic drugs at the desired time in the correct dosage to the correct site in the human body, pp. 1-9, date unknown but before the filing of this application.

Berry, Catherine C. et al., Potential Drug-Cell Delivery Routes Using Magnetic Nanoparticles, Centre for Cell Engineering, Glasgow University, European Cells and Materials vol. 6 Suppl. 2, 2003 p. 29.

http://www2.latech.edu/~ylvov/research/research.htm, Lvov, Yuri M., Nanofabrication of ordered multilayers by alternate absorption of polyions, nanoparticles and proteins: From planar films to microtemplates, Institute for Micromanufacturing, LaTech, Ruston, LA 71272, pp. 1-13, date unknown but before the filing of this application.

B. Thierry, et al., "Bioactive coatings of endovascular stents based on polyelectrolyte multilayers," *Biomacromolecules*. Nov.-Dec. 2003;4(6):1564-71.

* cited by examiner

MEDICAL ARTICLES HAVING REGIONS WITH POLYELECTROLYTE MULTILAYER COATINGS FOR REGULATING DRUG RELEASE

FIELD OF THE INVENTION

The present invention relates to medical articles which are useful for the controlled delivery of therapeutic agents.

BACKGROUND OF THE INVENTION

Medical articles are frequently used for delivery of therapeutic agents. For example, an implantable or insertable medical device, such as a stent or a catheter, may be provided with a polymer matrix coating layer that contains a therapeutic agent. Upon placement of the medical device at a desired location within a patient, the therapeutic agent is released from the polymer matrix and into the patient, thereby achieving a desired therapeutic outcome.

Such coatings, however, are frequently formed from relatively soft and tacky polymers, which may experience damage, for example, due to the mechanical forces that are exerted upon the medical device during loading and deployment of the same. In addition, where stents are utilized, unwanted polymer bridges can be created over the stent windows during stent deployment. Furthermore, where a biostable polymer is utilized as a coating material, an empty polymer shell remains after the drug has been eluted, which may be disadvantageous in some instances.

In contrast to most polymers used in for drug delivery, metallic structures (e.g., stainless steel and nitinol) and ceramic structures (e.g., aluminum oxide, titanium oxide and iridium oxide) are quite robust, resulting in excellent resistance against mechanical damage. Moreover, metallic and ceramic structures are frequently more biologically inert than polymers, and in some cases are biocompatible. Furthermore, metallic and ceramic structures can be made porous, thereby enabling them to hold large amounts of drugs. Unfortunately, drug release from porous structures is typically not well controlled.

The above and other challenges are addressed by the present invention.

SUMMARY OF THE INVENTION

According to one aspect of the present invention, medical articles (for instance, implantable or insertable medical devices such as catheters and stents, orthopedic implants, as well as innumerable others) are provided, which display controlled release of therapeutic agents that are disposed within them. The medical articles comprise: (a) a ceramic or metallic region whose surface comprises a plurality of depressions, (b) a multilayer coating region comprising multiple polyelectrolyte layers deposited over the surface of the ceramic or metallic region; and (c) a therapeutic agent disposed beneath or within the multilayer coating region. In some embodiments, the multilayer coating region extends into the surface depressions of the ceramic or metallic region. In some embodiments, the multilayer coating region extends over the depressions.

According to another aspect of the present invention, medical articles are provided, which display controlled release of therapeutic agents and which comprise the following: (a) a ceramic or metallic region, (b) a multilayer coating region comprising multiple polyelectrolyte layers deposited over the surface of the ceramic or metallic region, the multilayer coating region comprising a plurality of protuberances; and (c) a therapeutic agent disposed within regions beneath the protuberances.

As used herein, "depressions" are surface features that descend downward from the surrounding surface and include indentations, holes, pits, pores, dimples, valleys, troughs and furrows.

As used herein, "protuberances" are surface features that bulge outward from the surrounding surface and include bumps, ridges and other prominences. In many embodiments, the surface features are nanofeatures, which are defined herein as features that have at least one lateral surface dimension (e.g., the surface diameter for a circular pore, the surface width for a valley, the base diameter for a circular bump, the base width for a ridge, etc.) which is less than 500 nm. Features much larger than nanofeatures may also be present on the surface, in addition to the nanofeatures.

Other aspects of the present invention are direct to methods of making such medical articles, and to methods of releasing therapeutic agents into patients by contacting (e.g., adhering, implanting, inserting, etc.) the above medical articles with the patients.

An advantage of the present invention is that medical articles can be provided, which regulate the release of a therapeutic agent from the medical article to a patient.

Another advantage is that the present invention allows therapeutic agents to be provided in connection with porous structures having an essentially limitless range of pore sizes, while at the same time providing well-defined release profiles.

Another advantage of the present invention is that implantable or insertable medical articles can be provided that leave behind a ceramic or metallic structure, rather than a polymer, once the therapeutic agent is released from the medical article.

Yet another advantage of the present invention is that implantable or insertable medical articles can be provided which are robust against mechanical forces encountered during assembly and placement of the article in the body.

These and other aspects, embodiments and advantages of the present invention will become immediately apparent to those of ordinary skill in the art upon reading the disclosure to follow.

DETAILED DESCRIPTION OF THE INVENTION

According to an aspect of the present invention, a medical article is provided, which comprises the following: (a) a ceramic or metallic region whose surface comprises a plurality of depressions; (b) a multilayer coating region comprising multiple polyelectrolyte layers (also referred to herein as a "polyelectrolyte multilayer coating region") deposited over the surface of the ceramic or metallic region; and (c) a therapeutic agent disposed beneath or within the polyelectrolyte multilayer coating region.

In some embodiments, the multilayer coating region extends into the surface depressions of the ceramic or metallic region. In some embodiments, the multilayer coating region extends over the surface depressions, thereby providing enclosed cavities which are occupied by the therapeutic agent. In either case, therapeutic agent is disposed within the surface depressions. As a result, not only can increased quantities of therapeutic agent be loaded into the ceramic or metallic region (as compared, for example, to a smooth ceramic or metallic region), but also the depressions can act to regulate the release profile of the therapeutic agent from the medical article.

Medical articles benefiting from the present invention include any medical article for which controlled release of a therapeutic agent is desired. Examples of such medical articles include patches for delivery of therapeutic agent to intact skin, broken skin (including wounds), and surgical sites. Other examples of medical articles include implantable or insertable medical devices, for instance, catheters (e.g., renal or vascular catheters such as balloon catheters), guide wires, balloons, filters (e.g., vena cava filters), stents (including coronary vascular stents, cerebral, urethral, ureteral, biliary, tracheal, gastrointestinal and esophageal stents), stent grafts, cerebral aneurysm filler coils (including Guglilmi detachable coils and metal coils), vascular grafts, myocardial plugs, patches, pacemakers and pacemaker leads, heart valves, orthopedic implants, temporary implants in the mouth (e.g., temporarily crown jackets which release a pain killer), artificial implanted lenses and biopsy devices.

The medical articles of the present invention include medical articles that are used for either systemic treatment or for the localized treatment of any mammalian tissue or organ. Examples include tumors; organs including the heart, coronary and peripheral vascular system (referred to overall as "the vasculature"), lungs, trachea, esophagus, brain, liver, kidney, bladder, urethra and ureters, eye, intestines, stomach, pancreas, ovary, and prostate; skeletal muscle; smooth muscle; breast; dermal tissue; cartilage; and bone.

As used herein, "treatment" refers to the prevention of a disease or condition, the reduction or elimination of symptoms associated with a disease or condition, or the substantial or complete elimination a disease or condition. Preferred subjects are mammalian subjects and more preferably human subjects.

Medical articles having sustained releases profiles are beneficial in many cases. By "sustained release profile" is meant a release profile in which less than 25% of the total release from the medical article that occurs over the entire course of administration occurs after 1 day (or in some embodiments, after 2, 4, 6, 32, 64, 128 or even more days) of administration. Conversely, this means that more than 75% of the total release from the medical device will occur after the device has been administered for the same period.

The release characteristics that are ultimately of interest are, of course, the release characteristics within the subject, for example, within a mammalian subject. However, it is well known in the art to test the release characteristics within an experimental system that gives an indication of the actual release characteristics within the subject. For example, an aqueous buffer system such as Tris or PBS may be used for testing release of therapeutic agents from vascular medical devices.

The medical articles of the present invention comprise ceramic and/or metallic regions. Ceramic regions of the medical articles of the present invention typically comprise one or more of the following: metal oxides, including aluminum oxides and transition metal oxides (e.g., oxides of titanium, zirconium, hafnium, tantalum, molybdenum, tungsten, rhenium, and iridium); silicon-based ceramics, such as those containing silicon nitrides, silicon carbides and silicon oxides (sometimes referred to as glass ceramics); calcium phosphate ceramics (e.g., hydroxyapatite); and carbon-based, ceramic-like materials such as carbon nitrides.

Metallic regions of the medical articles of the present invention typically comprise one or more of the following: metal alloys such as cobalt-chromium alloys, nickel-titanium alloys (e.g., nitinol), cobalt-chromium-iron alloys (e.g., elgiloy alloys), nickel-chromium alloys (e.g., inconel alloys), and iron-chromium alloys (e.g., stainless steels, which contain at least 50% iron and at least 11.5% chromium), and noble metals such as silver, gold, platinum, palladium, iridium, osmium, rhodium, titanium, tungsten, and ruthenium.

In some embodiments, the ceramic or metallic region corresponds to only a portion of the medical article. For example, one or more ceramic or metallic coating regions can be (a) formed upon an underlying medical article substrate or (b) attached to an underlying medical article substrate (i.e., before or after the assembly of a multilayer polyelectrolyte coating region and/or before or after the introduction of a therapeutic agent as discussed further below). The ceramic or metallic coating region(s) can extend over all or a portion of the medical article substrate. For example, a ceramic or metallic coating region can be formed, which covers a single surface portion of the substrate and may be in any shape. As another example, multiple ceramic or metallic coating regions can be formed, which cover multiple surface portions of an underlying substrate (and may also be in any shape, e.g., in the form of a series of dots, rectangles, stripes, or any other pattern). In this way, several ceramic or metallic coating regions can be formed on a substrate surface, each with its own material composition, its own surface features, its own therapeutic agent and/or its own multilayer polyelectrolyte structure.

As a specific example, the porous ceramic region can correspond to an outward facing surface of a medical device that is in contact with body tissue, or to an outward facing surface of the device that is in contact with body fluid, like blood or the fluid inside the ear.

In other embodiments, the ceramic or metallic region corresponds to a distinct component of a medical article or to an entire medical article (e.g., where the ceramic or metallic region corresponds to a stent structure).

In some embodiments, the ceramic and metallic regions for use in accordance with the present invention have porous surfaces. The porous regions of the present invention include mesoporous regions (defined herein as porous regions having an average pore size ranging from 2-50 nanometers) and macroporous regions (defined herein as porous regions having an average pore size ranging from 50 nanometers to 5 microns or larger). Typically, the medical articles of the present invention contain porous regions that have an average pore size ranging from 1 to 100 nanometers, but can be much larger. For example, as discussed further below, pore sizes up to 100 micrometer are possible by using dissolvable structures (spheres, fibers) during the process of assembling the ceramic or metallic region.

Various techniques are known for producing porous ceramic structures in which the pore size can be adjusted from as little as about 0.3 nanometer to 3000 nanometers or larger. Where the pores sizes are in the nanometer range, these techniques are frequently able to exploit thermodynamic forces to drive the porous structures to an ordered state, including hexagonal porous structures, cubic porous structures, and many others.

For example, a variety of procedures are known for the production of mesoporous ceramic structures, many of which involve sol-gel techniques that utilize block copolymers as templates in order to create ceramic-polymer hybrid structures. The block copolymer is subsequently removed from the hybrid structures, for example, by thermal and/or chemical processes (e.g., by burning out the copolymer or by exposing the copolymer to a solvent), leaving behind a mesoporous ceramic structure.

As a specific example, Ulrich Wiesner at Cornell University has reported the fabrication of mesoporous ceramics using PI-b-PEO (poly[isoprene-b-ethylene oxide]) block copolymer as a template. Aluminosilicate sol-gel precursors are added to the copolymer. Due to thermodynamic forces, the resulting materials self-assemble into ordered structures based on the morphology of the copolymer. After heat treatment, the organics are burned off, leaving behind a porous ceramic material (alumina). This sol-gel method allows for variation in the final material composition. For example, pore morphologies reported by Dr. Wiesner's group include inverse hexagonal cylinder and "plumber's nightmare" morphologies. Dr. Wiesner's group is also working on incorporating magnetic particles into the mesoporous ceramics, which would allow for a material to be separated by size and by magnetic properties. For further information see, e.g., http://www.ccmr.cornell.edu/~uli/Pages/mesoporous.html.

As another specific example, researchers at MIT have produced nanoporous and nanorelief ceramic films having double gyroid morphology. In contrast to nanoporous materials, which contain tiny holes within the structure, nanorelief structures have interconnected struts that weave throughout the material. The gyroid shape is presently produced on a nanometer scale, because it is not possible to produce such materials through standard ceramic processing. The nanoporous and nanorelief structures are produced from self-assembling, block copolymer precursors. The process is a low temperature process, and only a single step is needed. Materials with complex, ordered pore structures are prepared by selecting block copolymers with certain volume fractions and phases to produce precursor materials with varying symmetries. By controlling the molecular weight the pore size and spacing can be specified. For further information, see, http://web.mit.edu/newsoffice/nr/1999/gyroid.html and Chan, V. Z.-H et al. "Ordered Bicontinuous Nanoporous and Nanorelief Ceramic Films from Self Assembling Polymer Precursors," *Science*, Nov. 26, 1999 v286 i5445 p.1716.

As another specific example, researchers at the Delft University of Technology have synthesized hierarchically structured nanoporous silica materials with two different pore sizes. Using their methodology, the two pore sizes can be independently controlled. This is accomplished by cross-linking primary nanostructured particles with a solution of triblock copolymers. This process forms secondary materials with a texture dependent on the reaction conditions (e.g., the type of copolymer, solvent, temperature, acidity and aging time). Ethanol is typically used as the solvent for the solution because it allows little change in the primary pore size. A compositional change in the template allows the secondary pore size distribution to be varied. The primary pore size is typically ranges between 15-20 nanometers, while the secondary pore size can be larger than 50 nanometers. See, e.g. Sun, J. and Coppens, M. O. "Synthesis of Hierarchically Structured Nanoporous Materials with a Controlled Bimodal Pore Size Distribution," presentation at Nanoscale Science and Engineering Topical Conference, November 2001.

Other methods of forming porous ceramic structures involve the formation of a colloid containing (a) ceramic nanopowder and (b) organic spheres, for example, polystyrene latex spheres, having a specified diameter, as template particles. The powder fills in around the spheres when the liquid portion of the colloid is evaporated. Subsequently, the organic spheres are removed (e.g., thermally or chemically) to create a porous structure. This process has been successful used, for example, to form 300 nanometer pores in titania, silica and alumina structures, which have overall dimensions on the order of several millimeters. The shrinkage that is observed using this method is much lower than with typically sol gel processes (e.g., 6 percent versus 30 percent for a typical sol gel process). For further information, see, e.g., Yi, Gi-Ra, et al., "Ordered Macroporous Particles by Colloidal Templating," *Chem. Mater.*, 2001, 13, 2613-2618.

Many techniques for the formation of porous ceramic structures, including those described above, are self-assembly approaches that require an alignment template about which the ceramic material is formed. Block copolymers, polystyrene spheres, water-in-oil emulsions, latex spheres, colloidal crystals and bioskeletons all are candidates for use as templates.

In some embodiments of the invention, different porosities are created over the medical article surface by using templates of different dimensions, for instance, by using different block copolymers in different sections of the medical article surface. As a specific example, in case of the Wiesner process discussed above, PI-b-PEO with different ratios of PI and PEO can be employed in different sections of the medical article. Such processes allow one to create regions having different release profiles in different sections of the medical article.

Other techniques for the formation of porous structures, however, do not require the use of templates. For example, sol-gel fabrication is beneficial from many standpoints, including low costs and flexibility in the control of film morphology. Singh, Grimes and Dickey have investigated the parameters (e.g., the effects of sol concentration, water/acid addition, humidity conditions) that influence the self-assembled fabrication of nanoporous ceramic films. More specifically, a sol-gel process was used to prepare the titania films, without a block copolymer or other template, and parameters such as those above were varied to test the effects. Through their efforts, they were able to produce a variety of nanoporous films. See, e.g., Singh, R. S., Grimes, C. A., Dickey, E. C. "Fabrication of nanoporous $TiO_2$ films through Bernard-Marangoni convection" *Materials Resources Innovations*. Aug. 18, 2001.

Figure 1:
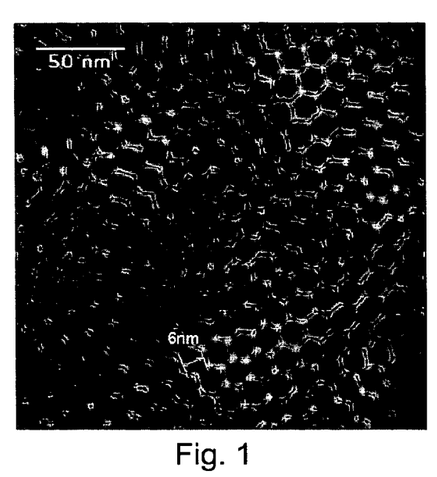
FIGS. 1 and 2 illustrate, respectively, hexagonal and cubic nanoporous titania structures, each having pore sizes on the order of 6 nm.
Figure 2:
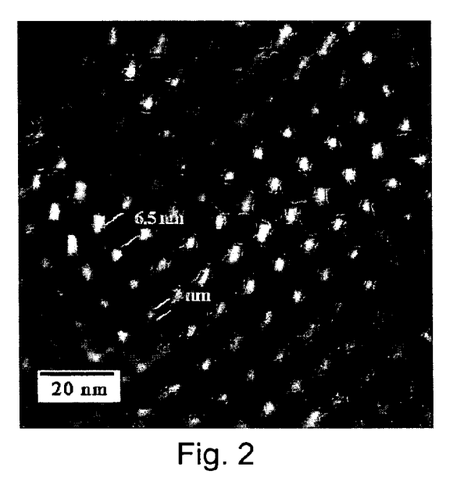

Dr. Abdelkrim Chemseddine from Hahn-Meitner Institut has also fabricated nanostructured materials through wet and sol-gel chemistries. His primary work is focused on the formation of nanostructured semiconducting films for use in solid state injection fuel cells. He has developed hexagonal and cubic nanoporous titania structures having pore sizes on the order of 6 nm. See, e.g., FIGS. 1 and 2 as well as http://www.hmi.de/people/chemseddine/group.htm for more information.

U.S. Pat. No. 6,399,528 entitled "Porous aluminum oxide structures and processes for their production" describes various ways to produce different pore sizes in alumina. In a first method, boehmite (colloidal aluminum monohydrate) is used as the raw material in a sol-gel process. The boehmite is dispersed in low pH distilled water. Subsequently, $ZrOCl_2 \cdot 8H_2O$ is added, and the sol is agitated and then poured into a glass shell. The material is dried, broken and sifted down to a particle size of 1-2 nanometers, after which it is sintered and subjected to an isothermal holding process. The resulting pore sizes range from an average of 56 nanometers at a sintering temperature of 1215° C. to 199 nanometers at a sintering temperature of 1370° C. At the same time, the percentage of open pores decreases slightly, i.e., from 41.2 percent to 40.5 percent. This procedure was also tried without the addition of the zirconia and it was found that the porosity was down to 36 percent after only sintering to 1200° C. The average pore size of 13 nanometers, however, was much smaller than in the case where zirconia was used. This procedure was further tried, without the addition of zirconia, using fine grain corundum alumina as the raw material, rather than boehmite, thereby assuring that the final product is 100 percent corundum alumina. The average open porosity in this procedure was 40.0 percent at different sintering temperatures. The average pore size was 51 nanometers.

This patent also explains how to produce macroporous alumina with pore sizes from 100-350 nanometers. In the procedure described, alumina with an average grain size of 0.5 microns and alumina with an average grain size of 1.4 microns are dispersed together with dispersing agents and distilled water. Zirconia is then added and the resulting mixture is milled. The milled mixture is then poured into a glass shell. The remaining preparation is the same as is described in the previous paragraph. Using this method, alumina with zirconia doping was found to have larger pores and a more highly porous corundum-type structure than alumina with no zirconia doping. Without doping, the open porosity of the alumina was 22.1% with an average pore size of 87 nanometers. With 4.5% zirconia doping, the open porosity the alumina was 51.0% with an average pore size of 315 nanometers.

It is also possible to create regions having pore sizes of different magnitude, for example, regions containing both nanometer-size and micrometer-size pores. For instance, in one embodiment, larger pore sizes are created by providing removable (e.g., dissolvable or sinterable) structures within the sol gel during the self-assembly process. Larger pore sizes are created upon the removal of the embedded structures, while nano-sized pores (mesoporousity) are created in the material surrounding the embedded structures by the sol-gel self-assembly process as described above.

Figure 6A:
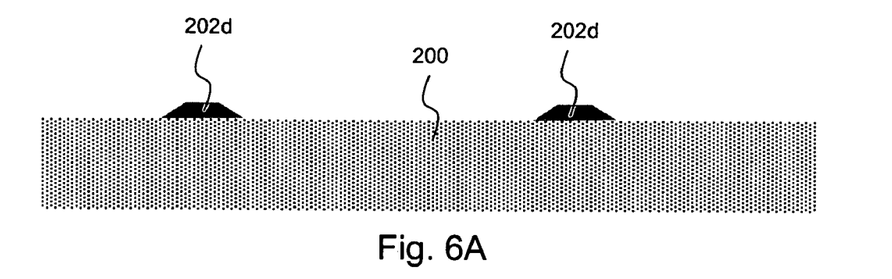
FIGS. 6A-6D illustrate a process for forming a medical article, in accordance with yet another embodiment of the present invention.
Figure 6B:
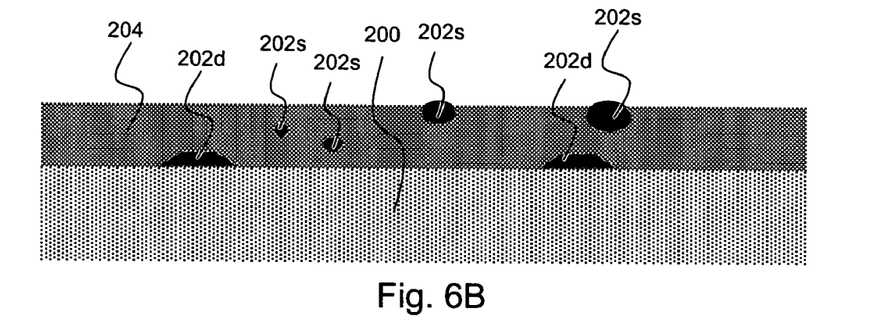
Figure 6C:
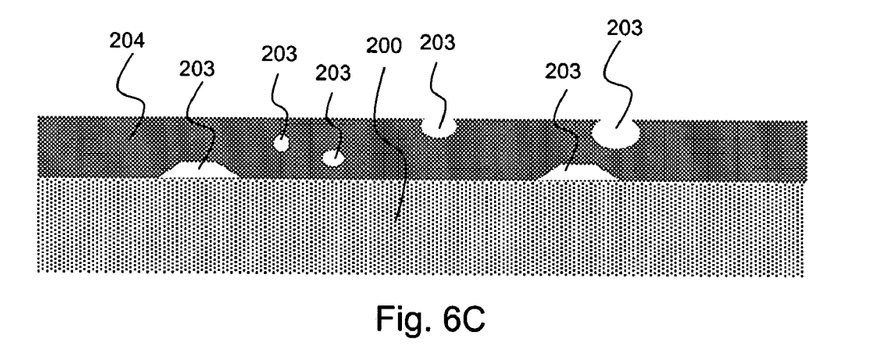
Figure 6D:
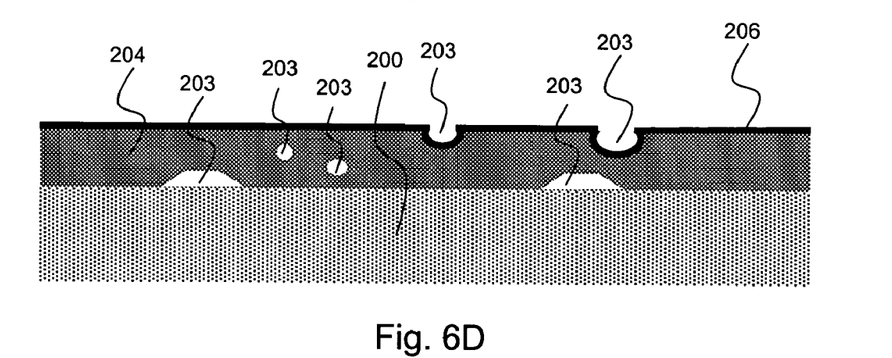

A specific example will now be described with reference to FIGS. 6A-6D. A substrate 200 is illustrated in FIG. 6A, which can be, for example, ceramic or metal, porous or solid. The substrate 200 is provided with dots 202$d$ of removable polymeric material, for example, using an ink jet printing technique. Subsequently, a sol such as those described above, which also contains spheres 202$s$ of removable polymeric material, is applied to the substrate 200, for example, by spraying, ultimately resulting in a self assembled sol-gel region 204 as illustrated in FIG. 6B. The polymeric material structures 202$s$, 202$d$ are then removed, for example, by dissolution or sintering. This results in large-sized (e.g., on the order of 1 to 100 microns) pores, or voids, 203, within a sol-gel region 104 that has nano-sized porosity, as illustrated in FIG. 6C. Finally a polyelectrolyte multilayer coating 206 is applied and the resulting medical article load with therapeutic agents, using techniques such as those discussed below, as shown in FIG. 6D.

In still other embodiments of the invention, depressions and/or through-holes are formed in a metallic or ceramic surface by means of a cutting, drilling or etching procedure. Specific examples include laser drilling/cutting techniques as well as wire EDM (electric discharge machining). As a more specific example, EDM can be used to produce holes (e.g., through holes or blind, potholes) in various metal surfaces. Using such techniques, depressions having a wide range of shapes and sizes can be created, including holes, trenches, and so forth. For instance, in FIGS. 3A and 4A, metallic or ceramic substrates 100 are provided with potholes 101 and through-holes 102, respectively.

Using techniques such as those above, as well as many others, ceramic and metallic bodies having a wide variety of surface depressions can be produced. Bodies having the overall shape that is desired can be produced in a number of ways, including machining and molding processes. Moreover, in many techniques, the precursor materials that ultimately form the porous regions are in fluid form and are thus amenable to fluid-based processing. For example, sol gel processes typically involve the transition of a system from a liquid "sol" (typically a colloidal liquid) to solid "gel." Thus, while in the liquid sol state, the material is amenable to fluid processing techniques such as spraying techniques, dipping techniques, roll and brush coating techniques, techniques involving coating via mechanical suspension such as air suspension, ink jet techniques, spin coating techniques, web coating techniques and combinations of these processes.

Once a ceramic or metallic region having the desired characteristics (e.g., material composition and porosity) is obtained, at least a portion of the surface of the ceramic or metallic region is used as a substrate for the assembly of one or more polyelectrolyte multilayer coating regions.

Polyelectrolyte multilayer coating regions can be assembled using various known layer-by-layer techniques. Layer-by-layer techniques involve coating various substrates using charged polymeric (polyelectrolyte) materials via electrostatic, self-assembly. In the layer-by-layer technique, a first polyelectrolyte layer having a first net charge is typically deposited on an underlying substrate, followed by a second polyelectrolyte layer having a second net charge that is opposite in sign to the net charge of the first polyelectrolyte layer, and so forth. The charge on the outer layer is reversed upon deposition of each sequential polyelectrolyte layer.

To the extent that the ceramic or metallic region does not have an inherent net surface charge, a surface charge may be provided. For example, where the region to be coated is conductive, the surface charge can be provided by applying an electrical potential to the same. Once a first polyelectrolyte layer is established in this fashion, a second polyelectrolyte layer having a second net charge that is opposite in sign to the net charge of the first polyelectrolyte layer can readily be applied, and so forth.

As another example, a surface charge can be provided by exposing the ceramic or metallic region to a charged amphiphilic substance. Amphiphilic substances include any substance having hydrophilic and hydrophobic groups. Where used, the amphiphilic substance should have at least one electrically charged group to provide the substrate surface with a net electrical charge. Therefore, the amphiphilic substance that is used herein can also be referred to as an ionic amphiphilic substance. Amphiphilic polyelectrolytes can be used as ionic amphiphilic substances. For example, a polyelectrolyte comprising charged groups (which are hydrophilic) as well as hydrophobic groups, such as polyethylenimine (PEI) or poly(styrene sulfonate) (PSS), can be employed. Cationic and anionic surfactants can also be used as amphiphilic substances. Cationic surfactants include quaternary ammonium salts ($R_4N^+X^-$), for example, didodecyldimethylammonium bromide (DDDAB), alkyltrimethylammonium bromides such as hexadecyltrimethylammonium bromide (HTAB), dodecyltrimethylammonium bromide (DTMAB), myristyltrimethylammonium bromide (MTMAB), or palmityl trimethylammonium bromide, or N-alkylpyridinium salts, or tertiary amines ($R_3NH^+X^-$), for example, cholesteryl-3β-N-(dimethyl-aminoethyl)-carbamate or mixtures thereof, wherein $X^{31}$ is a counter-anion, e.g. a halogenide. Anionic surfactants include alkyl or olefin sulfate ($R-OSO_3M$), for example, a dodecyl sulfate such as sodium dodecyl sulfate (SDS), a lauryl sulfate such as sodium lauryl sulfate (SLS), or an alkyl or olefin sulfonate ($R-SO_3M$), for example, sodium-n-dodecyl-benzene sulfonate, or fatty acids ($R-COOM$), for example, dodecanoic acid sodium salt, or phosphoric acids or cholic acids or fluoro-organics, for example, lithium-3-[2-(perfluoroalkyl)ethylthio]propionate or mixtures thereof, where R is an organic radical and M is a counter-cation.

In other embodiments, a surface charge is provided by adsorbing cations (e.g., protamine sulfate, polyallylamine, polydiallyldimethylammonium species, polyethyleneimine, chitosan, gelatin, spermidine, albumin, among others) or anions (e.g., polyacrylic acid, sodium alginate, polystyrene sulfonate, eudragit, gelatin (gelatin is an amphoteric polymer, hence it fits in both categories depending how it is being prepared), hyaluronic acid, carrageenan, chondroitin sulfate, carboxymethylcellulose, among others) to the surface of the ceramic or metallic region as a first charged layer. Although full coverage may not be obtained for the first layer, once several layers have been deposited, a full coverage should ultimately be obtained, and the influence of the substrate is expected to be negligible. The feasibility of this process has been demonstrated on glass substrates using charged polymeric (polyelectrolyte) materials. See, e.g., "Multilayer on solid planar substrates," *Multi-layer thin films, sequential assembly of nanocomposite materials*, Wiley-VCH ISBN 3-527-30440-1, Chapter 14; and "Surface-chemistry technology for microfluidics," Hau, Winky L. W. et al. *J. Micromech. Microeng.* 13 (2003) 272-278.

The species for establishing surface charge can be applied to the ceramic or metallic region by a variety of techniques. These techniques include, for example, spraying techniques, dipping techniques, roll and brush coating techniques, techniques involving coating via mechanical suspension such as air suspension, ink jet techniques, spin coating techniques, web coating techniques and combinations of these processes.

Once a sufficiently charged substrate is obtained, it can be coated with a layer of an oppositely charged polyelectrolyte. Multilayers are formed by repeated treatment with alternating oppositely charged polyelectrolytes, i.e., by alternating treatment with cationic and anionic polyelectrolytes. The polymer layers self-assemble by means of electrostatic layer-by-layer deposition, thus forming a multilayered polyelectrolyte coating over the ceramic or metallic region.

Polyelectrolytes are polymers having charged (e.g., ionically dissociable) groups. Usually, the number of these groups in the polyelectrolytes is so large that the polymers in dissociated form (also called polyions) are water-soluble. Depending on the type of dissociable groups, polyelectrolytes are typically classified as polyacids and polybases. When dissociated, polyacids form polyanions, with protons being split off. Polyacids include inorganic, organic and biopolymers. Examples of polyacids are polyphosphoric acids, polyvinylsulfuric acids, polyvinylsulfonic acids, polyvinylphosphonic acids and polyacrylic acids. Examples of the corresponding salts, which are also called polysalts, are polyphosphates, polyvinylsulfates, polyvinylsulfonates, polyvinylphosphonates and polyacrylates. Polybases contain groups which are capable of accepting protons, e.g., by reaction with acids, with a salt being formed. Examples of polybases having dissociable groups within their backbone and/or side groups are polyallylamine, polyethylimine, polyvinylamine and polyvinylpyridine. By accepting protons, polybases form polycations.

Suitable polyelectrolytes according to the invention include those based on biopolymers, for example, alginic acid, gummi arabicum, nucleic acids, pectins and proteins, chemically modified biopolymers such as carboxymethyl cellulose and lignin sulfonates, and synthetic polymers such as polymethacrylic acid, polyvinylsulfonic acid, polyvinylphosphonic acid and polyethylenimine. Linear or branched polyelectrolytes can be used. Using branched polyelectrolytes can lead to less compact polyelectrolyte multilayers having a higher degree of wall porosity. Polyelectrolyte molecules can be crosslinked within or/and between the individual layers, e.g. by crosslinking amino groups with aldehydes, for example, to increase stability. Furthermore, amphiphilic polyelectrolytes, e.g. amphiphilic block or random copolymers having partial polyelectrolyte character, can be used to affect permeability towards polar small molecules. Such amphiphilic copolymers consist of units having different functionality, e.g. acidic or basic units, on the one hand, and hydrophobic units, on the other hand (e.g., polystyrenes, polydienes or polysiloxanes), which can be present in the polymer as blocks or distributed statistically.

Suitable polyelectrolytes include low-molecular weight polyelectrolytes (e.g., polyelectrolytes having molecular weights of a few hundred Daltons) up to macromolecular polyelectrolytes (e.g., polyelectrolytes of biological origin, which commonly have molecular weights of several million Daltons).

Specific examples of polycations include protamine sulfate polycations, poly(allylamine) polycations (e.g., poly(allylamine hydrochloride) (PAH)), polydiallyldimethylammonium polycations, polyethyleneimine polycations, chitosan polycations, gelatin polycations, spermidine polycations and albumin polycations. Specific examples of polyanions include poly(styrenesulfonate) polyanions (e.g., poly(sodium styrene sulfonate) (PSS)), polyacrylic acid polyanions, sodium alginate polyanions, eudragit polyanions, gelatin polyanions, hyaluronic acid polyanions, carrageenan polyanions, chondroitin sulfate polyanions, and carboxymethylcellulose polyanions.

By using polyelectrolytes that are biodisintegrable, the release of the therapeutic agent can be further controlled based on the rate of disintegration of the polyelectrolyte layers. Moreover, as indicated above, implantable or insertable medical articles containing a biodisintegrable multilayer polyelectrolyte coating leave behind only the underlying ceramic or metallic structure once the therapeutic agent is released from the medical article. As used herein, a "biodisintegrable" material is a material which undergoes dissolution, degradation, resorption and/or other disintegration processes upon administration to a patient. Examples of biodisintegrable polyelectrolytes include polyglycolic acid (PGA), polylactic acid (PLA), polyamides, poly-2-hydroxybutyrate (PHB), polycaprolactone (PCL), poly(lactic-co-glycolic)acid (PLGA), protamine sulfate, polyallylamine, polydiallyldimethylammonium species, polyethyleneimine, chitosan, eudragit, gelatin, spermidine, albumin, polyacrylic acid, sodium alginate, polystyrene sulfonate, hyaluronic acid, carrageenan, chondroitin sulfate, carboxymethylcellulose, heparin, other polypeptides and proteins, and DNA, among others.

As with species for establishing surface charge (described above), the polyelectrolyte layers can be applied to the ceramic or metallic region by a variety of techniques including, for example, spraying techniques, dipping techniques, roll and brush coating techniques, techniques involving coating via mechanical suspension such as air suspension, ink jet techniques, spin coating techniques, web coating techniques and combinations of these processes.

It is noted that the polyelectrolyte species (or the species for establishing surface charge, as the case may be) need not be applied to all of the available ceramic or metallic surface, but may cover only a portion of the substrate. For example, a single polyelectrolyte multilayer coating region can be formed, which covers a single surface portion of the ceramic or metallic region and may be in any shape. As another example, multiple polyelectrolyte multilayer coating regions can be formed, which cover multiple surface portions of the ceramic or metallic region (and may also be in any shape, e.g., in the form of a series of dots, stripes, or any other pattern). In this way, several polyelectrolyte multilayer coating regions can be formed on the ceramic or metallic surface region(s), each with a distinct number of polyelectrolyte layers and/or with different polyelectrolyte species forming the layers.

The total thickness of the polyelectrolyte multilayer coating region that is assembled will frequently range, for example, from 4 to 1000 nm. For example, a typical PAH/PSS single layer thickness is 1.5 nm. For proteins, however, much larger thickness are frequently encountered. Moreover, one can substitute a layer of charged nanoparticles (e.g., iron oxide, titania, gold, etc.) for a polyelectrolyte layer to achieve much greater wall thicknesses.

So long as the size of the surface pores (or other surface depressions) in the ceramic or metallic structure are well beyond the thickness of the polyelectrolyte layers, one is able to coat not only the outside of the ceramic or metallic region, but also to extend the polyelectrolyte multilayer coating into the pores of the ceramic or metallic region as well. It is noted that, where the pore size is of the same order of magnitude as the polyelectrolyte multilayer coating thickness, it is only possible to add so many polyelectrolyte layers before closing the pores. However, one can nonetheless continue to add layers to the outside of the ceramic or metallic structure, even after the pores are closed. The closure of the pores and continued layer deposition offers a unique way to create a step function in the drug release. Specifically, once the outer layers are dissolved and the porous structure is opened, a sudden increase in surface area is available, leading to an increase in the rate of drug release.

As noted above, at least one therapeutic agent is disposed beneath and/or within the polyelectrolyte multilayer coating in the medical articles of the present invention. Several techniques are available for doing so.

In some embodiments, the depressions within the ceramic or metallic region are filled with therapeutic agent prior to application of the polyelectrolyte multilayer coating. For example, in some instances, the depressions of the ceramic or metallic region are first filled with a therapeutic agent of relatively low water solubility, allowing a polyelectrolyte multilayer coating to be applied from an aqueous solution with relatively low loss of therapeutic.

In some embodiments, the therapeutic agent is charged, for example, because it is itself a charged molecule or because it is intimately associated with a charged molecule. Examples of charged therapeutic agents include small molecule and polymeric therapeutic agents containing ionically dissociable groups, for example, therapeutic agents containing carboxylic, phosphonic, phosphoric, sulfuric, sulfonic, or other acid groups, or therapeutic agents containing amine, imine or another basic groups. As noted above, acidic groups generally become anionic groups in aqueous solution by donating protons, while basic groups generally become cations by accepting protons. In some cases, the therapeutic agent will contain both acidic and basic groups, yet will have a net overall charge. Examples of charged therapeutic agents include polynucleotides (e.g., DNA and RNA) and polypeptides (e.g., proteins, whose overall net charge will vary with pH, based on their respective isoelectric points), among others. For example, insulin is a negatively charged molecule at neutral pH, while protamine is positively charged.

Even where the therapeutic agent does not possess one or more charged groups, it can nevertheless be provided with a charge, for example, through non-covalent association with a charged species. Examples of non-covalent associations include hydrogen bonding, hydrophilic/lipophilic interactions, and so forth. For instance, in accordance with one specific embodiment, the therapeutic agent is associated with an ionic amphiphilic substance, such as one of those set forth above.

In certain embodiments where a charged therapeutic agent is employed (e.g., by being inherently charged or by associating with a charged species), it is adsorbed to the surface of the ceramic or metallic region, thereby providing the ceramic or metallic region with an initial surface charge (and thus setting the stage for the deposition of a series of polyelectrolyte layers over the charged therapeutic agent in subsequent steps). In others of these embodiments, one or more layers of the charged therapeutic agent is/are deposited over the ceramic or metallic region during the course of assembling the polyelectrolyte multilayer coating. For example, in some instances, the therapeutic agent is itself a polyelectrolyte (e.g., where the therapeutic agent is a polypeptide or a polynucleotide) and it is used as such to create one or more of the polyelectrolyte layers within the multilayer coating. In other instances, the charged therapeutic agent is not a polyelectrolyte (e.g., it may be a charged small molecule drug). Nevertheless, one or more layers of the charged therapeutic agent can be substituted for one or more polyelectrolyte layers of the same net charge (i.e., positive or negative) during the multilayer assembly process. In each of the above cases the therapeutic agent is disposed beneath and/or within the polyelectrolyte multilayer coating.

In other embodiments, the polyelectrolyte multilayer coating is loaded with therapeutic agent subsequent to its formation. In this regard, various techniques have been reported in the literature for incorporating therapeutic agents into preformed microscopic polyelectrolyte multilayer capsules, and these techniques are equally applicable to the microscopic or macroscopic polyelectrolyte-multilayer-coated ceramic or metallic structures of the present invention.

For example, techniques are known in the polyelectrolyte multilayer art for increasing the porosity, and thus the permeability, of the multilayer. For instance, techniques have been reported for introducing different materials into polyelectrolyte multilayer capsules by varying the pH. In particular, polyelectrolyte multilayer structures are known (e.g. PSS-PAH multilayer structures) which are effectively closed at higher pH's. However, at more acidic pH's (e.g., pH 6 and below) the multilayer structures open up, allowing macromolecules (e.g., FITC-labeled dextran, MW~75,000 and MW~2,000,000 as well as FITC-labeled albumin) to freely permeate the capsule. See, e.g., Antipov, A. A. et al., "Polyelectrolyte multilayer capsule permeability control," *Colloids and Surfaces A: Physicochemical and Engineering Aspects*, 198-200 (2002) pp. 535-541.

In general, and without wishing to be bound by theory, there are at least two ways in which therapeutic agents are positioned within the polyelectrolyte multilayer covered ceramic or metallic structures of the present invention using such techniques. For example, in instances where the pore sizes are sufficiently small such that they are closed by the deposition of the polyelectrolyte layers, fully enclosed pockets can be created. The therapeutic agent can thus be introduced into these pockets by lowering the pH value as is discussed above in connection with polyelectrolyte multilayer enclosed capsules. On the other hand, in the case of larger pores, where an open pore structure remains, the therapeutic agent can nonetheless positioned in between and/or beneath the polyelectrolyte layers.

In other embodiments, surface depressions in metallic or ceramic materials are filled with a removable materials, followed by: (a) deposition of a polyelectrolyte multilayer coating, (b) removal of removal of the removable material and (c) introduction of a therapeutic agent. For example, it is known to encapsulate particles with a polyelectrolyte multilayer shell, followed by at least partially disintegration of the thus encapsulated particles without destroying the shell. See, e.g., U.S. patent application Ser. No. 20003/0175517 to Voight et al., S. Moya et al, "Polyelectrolyte multilayer capsules templated on biological cells: core oxidation influences layer chemistry," *Colloids and Surfaces A: Physicochem. Eng. Aspects,* 183-185 (2001), pp. 27-40.

Figure 3A:
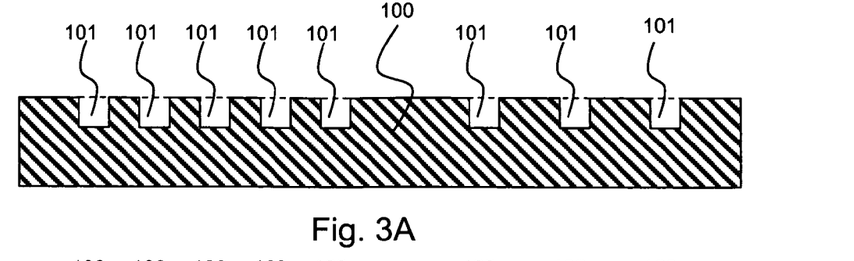
FIGS. 3A-3E illustrate a process for forming a medical article, in accordance with an embodiment of the present invention.
Figure 3B:
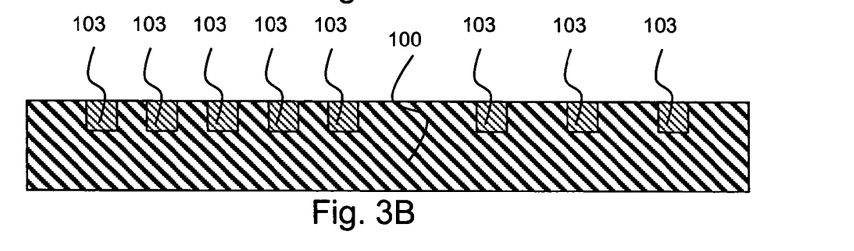
Figure 4A:
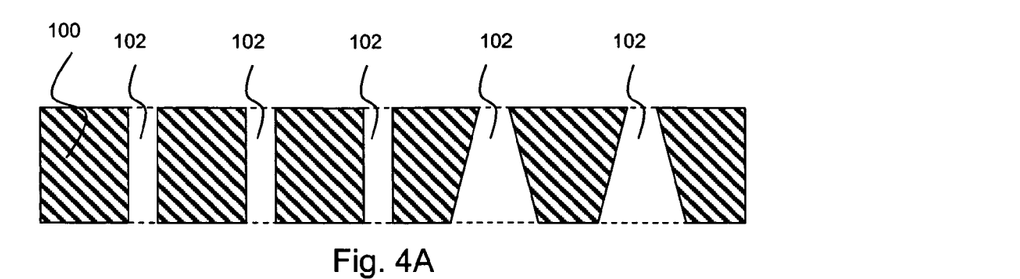
FIGS. 4A-4E illustrate a process for forming a medical article, in accordance with another embodiment of the present invention.
Figure 4B:
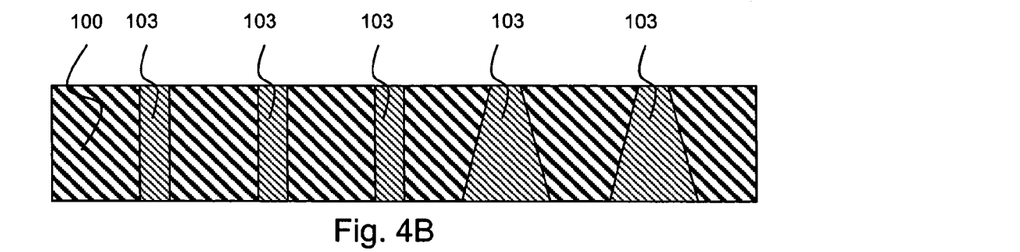

According to an embodiment of the present invention, and with reference to FIGS. 3A-E and 4A-E, a disintegrable material 103 is inserted into the potholes 101 of substrate 100 illustrated in FIG. 3A or the through-holes 102 of substrate 100 illustrated in FIG. 4A. The resulting structures are illustrated in FIGS. 3B and 4B, respectively. An example of a disintegrable material is partly cross-linked melamine-formaldehyde. Partly cross-linked melamine-formaldehyde, which is described in WO 99/47252, can be dissolved by adjusting the pH in the surrounding medium to an acidic value, while the polyelectrolyte multilayer coating remains intact. Partly cross-linked melamine-formaldehyde particles can also be dissolved by chemical reactions, for example, by sulfonation in aqueous media. Other examples of disintegrable materials include urea formaldehyde, salts such as carbonate compounds whose solubility in aqueous solutions can be adjusted, and organic compounds that are insoluble in water but soluble in organic solvents such as ethanol, for example, cyanine dyes. Still other disintegrable materials include amphiphilic materials, for example, phospholipids, as well as proteins and lipids, which can be disintegrated by adding lysis reagents, for instance peroxo compounds such as $H_2O_2$ or/and hypochlorite compounds such as sodium or potassium hypochlorite.

Figure 3C:
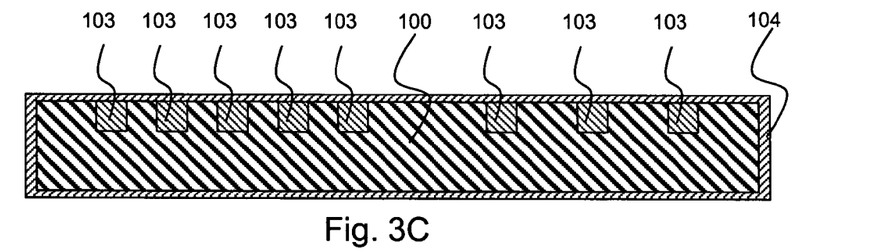
Figure 4C:
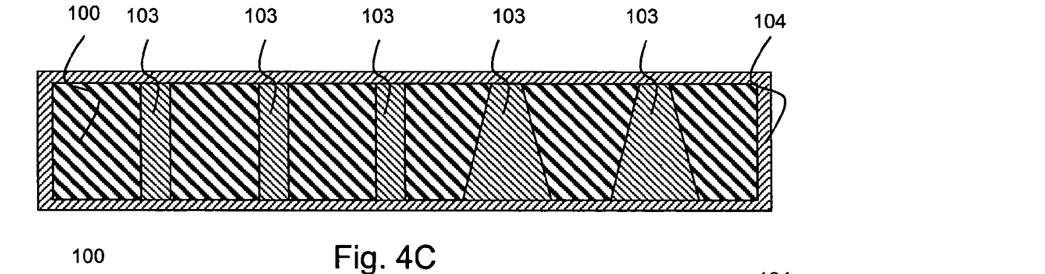

The structures of FIGS. 3B and 4B are then provided with a polyelectrolyte multilayer coating 104, for example, using the techniques such as those described above. The resulting structures are illustrated in FIGS. 3C and 4C, respectively.

Figure 3D:
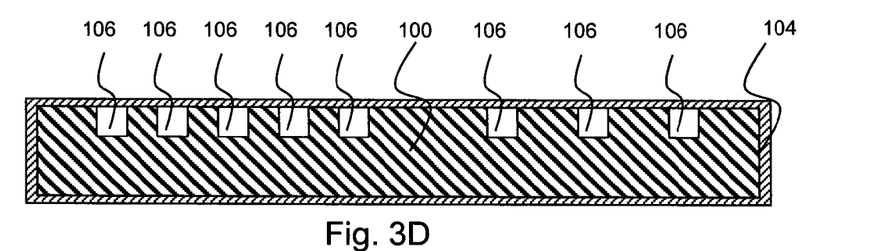
Figure 4D:
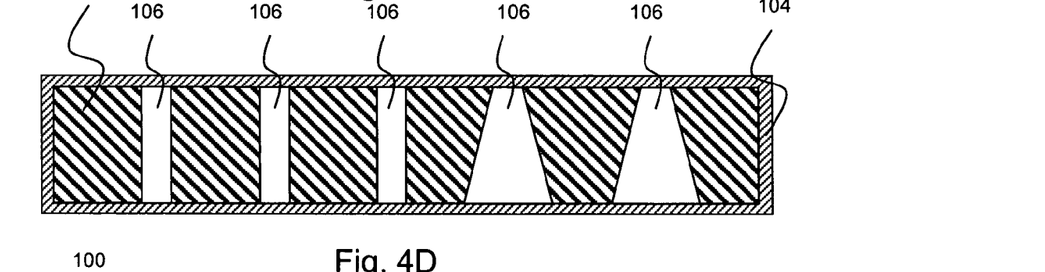

Subsequently, the disintegrable material 103 is removed, resulting in enclosed cavities 106 as illustrated in FIGS. 3D and 4D, respectively. In some cases, the disintegration products of the disintegrable material (e.g., dissolved species or species fragments, such as the oligomers that are formed when partly cross-linked melamine-formaldehyde particles are disintegrated) will escape from the inside of the cavities 106 through nanopores that are inherent in the polyelectrolyte multilayer coating 104. In other instances, escape of the disintegration products is assisted by varying the pH of the surrounding medial. For example, as discussed above, certain polyelectrolyte multilayer structures 104 are known (e.g. PSS-PAH multilayer structures) which are effectively closed at higher pHs, but whose structures open up at more acidic pHs.

Figure 3E:
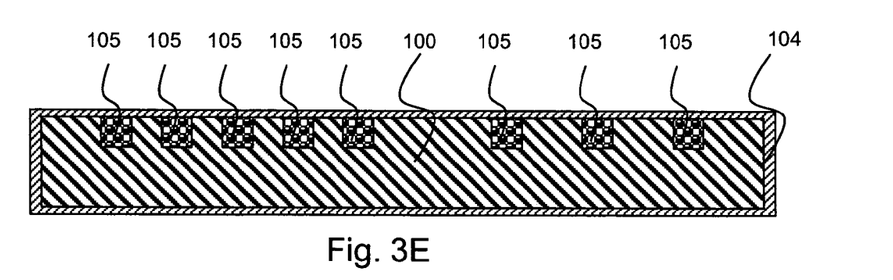
Figure 4E:
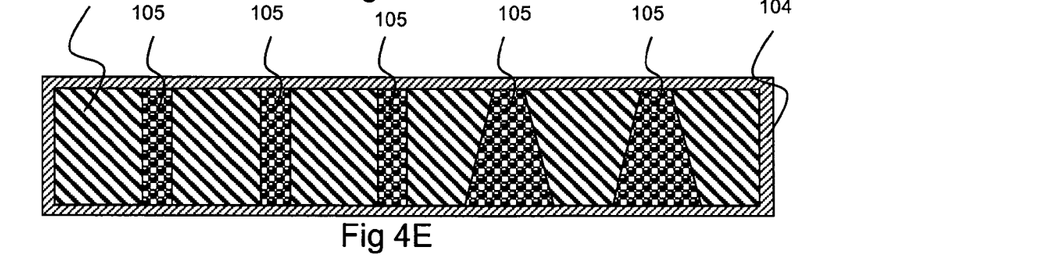

In a next step, the cavities 106 created above are filled with therapeutic agent. The structures are illustrated in FIGS. 3E and 4E, respectively, subsequent to filling the cavities with therapeutic agent 105. For example, the variation of pH to open and close the polyelectrolyte multilayer, thereby allowing the cavities to be fill with therapeutic agent, is described above. Other techniques are also known in which polyelectrolyte capsules are loaded by taking advantage of gradients across the capsule wall to effect precipitation or synthesis of a desired substance within the shell. These techniques are also applicable to the process of filling cavities 106. As a general rule, large macromolecules typically cannot penetrate polyelectrolyte multilayers, while small molecules, on the other hand, can. Accordingly, the presence of macromolecules inside the cavities can lead to a difference in the physicochemical properties between the inside and the outside of the cavity, for example, providing gradients in pH and/or polarity that can be used to trap materials within the cavities.

In this regard, capsules have been made by means of layer-by-layer adsorption of oppositely charged polyelectrolytes (i.e., an outer shell of alternating PAH and PSS) on a $yttrium^{3+}$/PSS inner shell, which is further disposed on the surface of a colloidal template particle (i.e., melamine formaldehyde particles). Subsequently, the melamine formaldehyde core is removed, followed by the decomposition of the $Yttrium^{3+}$/PSS inner shell. A solution of a poorly water-soluble drug in an organic solvent (e.g., acetone) is then mixed with a water suspension of the capsules and diluted with acetone until complete dissolution of the drug is achieved. The organic solvent is then allowed to evaporate. The presence of the free polyelectrolyte molecules in the core results in a higher water concentration within the core, relative to the bulk. Because the concentration of water is higher in the core than in the bulk, the drug precipitates within the core, producing a drug-loaded capsule. Additional information can be found, for example, in "A Novel Method for Encapsulation of Poorly Water-soluble Drugs: Precipitation in Polyelectrolyte Multilayer Shells," I. L. Radtchenko et al., *International Journal of Pharmaceutics,* 242, 219-223 (2002), the disclosure of which is hereby incorporated by reference. Hence, by depositing a $yttrium^{3+}$/PSS inner shell (not illustrated) over the disintegrable material 103 prior to deposition of the multilayer 104, the above technique is used to load the cavities with poorly water-soluble therapeutic agents 105.

As another example, the selective inorganic synthesis of magnetite ($Fe_3O_4$) inside poly(styrene sulfonate)/poly(allylamine hydrochloride polyelectrolyte capsules of micron scale as been reported. Micron and submicron sized capsules are made by means of layer-by-layer adsorption of oppositely charged polyelectrolytes (PSS, PAH) on the surface of colloidal template particles (e.g., weakly cross-linked melamine formaldehyde particles having a precipitated PAH-citrate complex) with subsequent degradation of the template core. This leaves free PAH in the core, which creates a pH gradient across the shell. At this point, (a) negatively charged, pre-formed magnetic particles of sufficiently small size (e.g., $Fe_3O_4$ nanoparticles) are used to impregnate the capsules whereupon they are held by electrostatic interactions, or (b) magnetic material (e.g., $Fe_3O_4$) can be selectively synthesized inside the core based on the pH gradient and on presence of dissolved PAH in the capsule. Additional information can be found, for example, in "Micron-Scale Hollow Polyelectrolyte Capsules with Nanosized Magnetic $Fe_3O_4$ Inside,"

*Materials Letters*, D. G. Shchukin et al. (in press), the disclosure of which is hereby incorporated by reference. Thus, by providing the disintegrable material 103 in the structures of FIGS. 3B and 4B with a precipitated PAH-citrate complex, and by substituting therapeutic agent for the magnetite, the above technique is used to load the cavities with therapeutic agents 105.

In accordance with another aspect of the present invention, medical articles are provided, which comprise the following: (a) a ceramic or metallic region, (b) a multilayer coating region comprising multiple polyelectrolyte layers deposited over a surface of the ceramic or metallic region, the multilayer coating region comprising a plurality of protuberances; and (c) a therapeutic agent disposed within regions beneath the protuberances. One example of such a structure is illustrated in FIG. 7, which illustrates the ceramic or metallic region 100, the polyelectrolyte multilayers 104, the protuberances 104p, beneath which is disposed the therapeutic agent 105.

Figure 5A:
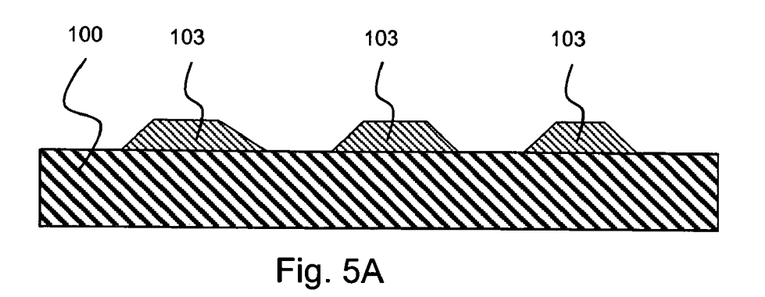
FIGS. 5A-5D illustrate a process for forming a medical article, in accordance with still another embodiment of the present invention.
Figure 5B:
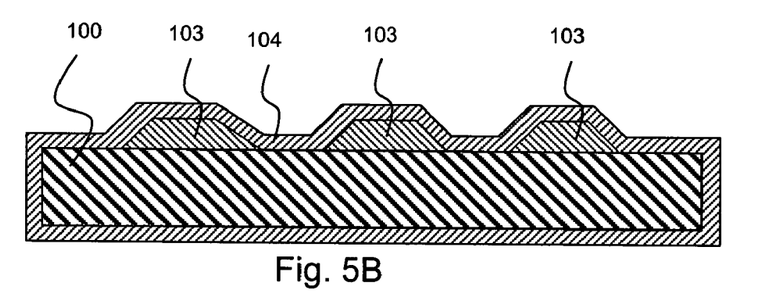
Figure 5C:
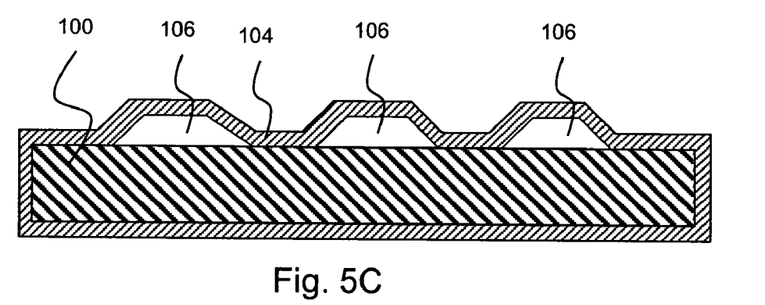
Figure 5D:
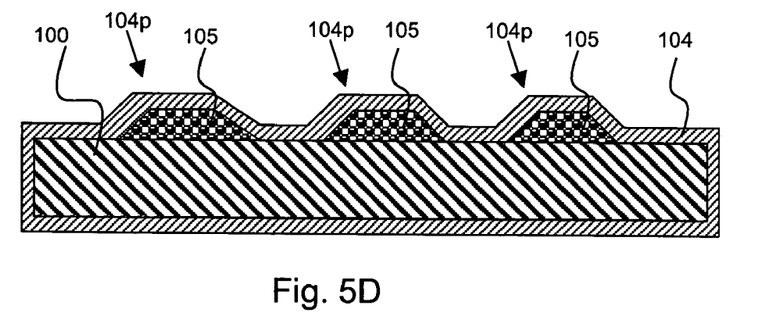
Figure 7:
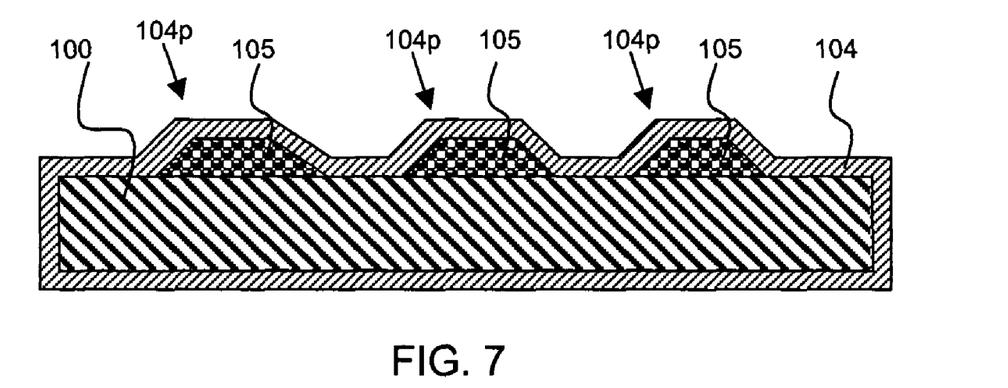
FIG. 7 illustrates a structure in accordance with an embodiment of the present invention.

In accordance with an embodiment of the present invention, the structure of FIG. 7 is created using a process very much like the process that is used to create the structures of FIGS. 3E and 4E. For example, turning now to FIGS. 5A-5D, a metallic or ceramic region 100 is provided with multiple regions 103 (e.g., dots) of disintegrable material such as those discussed above, for example, by spraying through at mask, by ink jet techniques, or by laying down a polymer layer and removing part of it, for example, using laser ablation at 248 nm or 193 nm. The resulting structure is illustrated in FIG. 5A. This structure is then provided with a polyelectrolyte multilayer coating 104, for example, using the techniques described above. The resulting structure is illustrated in FIG. 5B. Subsequently, the disintegrable material regions 103 are removed as previously discussed, resulting in enclosed pockets 106 as illustrated in FIG. 5C. Finally, the pockets 106 created in the prior step are filled with therapeutic agent 105 as illustrated in FIG. 5D, using techniques such as those discussed above.

Therapeutic agents may be used singly or in combination in the medical articles of the present invention. "Drugs," "therapeutic agents," "pharmaceutically active agents," "pharmaceutically active materials," and other related terms may be used interchangeably herein. These terms include genetic therapeutic agents, non-genetic therapeutic agents and cells.

Exemplary non-genetic therapeutic agents for use in connection with the present invention include: (a) anti-thrombotic agents such as heparin, heparin derivatives, urokinase, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promotors; (g) vascular cell growth inhibitors such as growth factor inhibitors, growth factor receptor antagonists, transcriptional repressors, translational repressors, replication inhibitors, inhibitory antibodies, antibodies directed against growth factors, antibodies recognizing receptors on endothelial progenitor cells, proteins of the tetraspanin family, such as CD9 Beta-1 and Beta-3 integrins, CD63, CD81, FcgammaRII, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; (o) agents that interfere with endogenous vasoactive mechanisms; (p) inhibitors of leukocyte recruitment, such as monoclonal antibodies; (q) cytokines; and (r) hormones.

Preferred non-genetic therapeutic agents include paclitaxel, sirolimus, everolimus, tacrolimus, dexamethasone, estradiol, ABT-578 (Abbott Laboratories), trapidil, liprostin, Actinomcin D, Resten-NG, Ap-17, abciximab, clopidogrel and Ridogrel.

Exemplary genetic therapeutic agents for use in connection with the present invention include anti-sense DNA and RNA as well as DNA coding for the various proteins (as well as the proteins themselves): (a) anti-sense RNA, (b) tRNA or rRNA to replace defective or deficient endogenous molecules, (c) angiogenic and other factors including growth factors such as acidic and basic fibroblast growth factors, vascular endothelial growth factor, endothelial mitogenic growth factors, epidermal growth factor, transforming growth factor $\alpha$ and $\beta$, platelet-derived endothelial growth factor, platelet-derived growth factor, tumor necrosis factor $\alpha$, hepatocyte growth factor and insulin-like growth factor, (d) cell cycle inhibitors including CD inhibitors, and (e) thymidine kinase ("TK") and other agents useful for interfering with cell proliferation. Also of interest is DNA encoding for the family of bone morphogenic proteins ("BMP's"), including BMP-2, BMP-3, BMP-4, BMP-5, BMP-6 (Vgr-1), BMP-7 (OP-1), BMP-0, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Vectors for delivery of genetic therapeutic agents include viral vectors such as adenoviruses, gutted adenoviruses, adeno-associated virus, retroviruses, alpha virus (Semliki Forest, Sindbis, etc.), lentiviruses, herpes simplex virus, replication competent viruses (e.g., ONYX-015) and hybrid vectors; and non-viral vectors such as artificial chromosomes and mini-chromosomes, plasmid DNA vectors (e.g., PCOR), cationic polymers (e.g., polyethyleneimine, polyethyleneimine (PEI)), graft copolymers (e.g., polyether-PEI and polyethylene oxide-PEI), neutral polymers PVP, SP1017 (SUPRATEK), lipids such as cationic lipids, liposomes, lipoplexes, nanoparticles, or microparticles, with and without targeting sequences such as the protein transduction domain (PTD).

Cells for use in connection with the present invention include cells of human origin (autologous or allogeneic), including whole bone marrow, bone marrow derived mononuclear cells, progenitor cells (e.g., endothelial progenitor cells), stem cells (e.g., mesenchymal, hematopoietic, neuronal), pluripotent stem cells, fibroblasts, myoblasts, satellite cells, pericytes, cardiomyocytes, skeletal myocytes or macrophage, or from an animal, bacterial or fungal source (xenogeneic), which can be genetically engineered, if desired, to deliver proteins of interest.

Numerous therapeutic agents, not necessarily exclusive of those listed above, have been identified as candidates for vascular treatment regimens, for example, as agents targeting restenosis. Such agents are useful for the practice of the present invention and include one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/Guanylate cyclase stimulants such as forskolin, as well as adenosine analogs, (d) catecholamine modulators including α-antagonists such as prazosin and bunazosine, β-antagonists such as propranolol and α/β-antagonists such as labetalol and carvedilol, (e) endothelin receptor antagonists, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) ACE inhibitors such as cilazapril, fosinopril and enalapril, (h) ATII-receptor antagonists such as saralasin and losartan, (i) platelet adhesion inhibitors such as albumin and polyethylene oxide, (j) platelet aggregation inhibitors including aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and β-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (o) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, fluvastatin, simvastatin and cerivastatin, (u) fish oils and omega-3-fatty acids, (v) free-radical scavengers/antioxidants such as probucol, vitamins C and E, ebselen, trans-retinoic acid and SOD mimics, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-βpathway agents such as polyanionic agents (heparin, fucoidin), decorin, and TGF-βantibodies, EGF pathway agents such as EGF antibodies, receptor antagonists and chimeric fusion proteins, TNF-αpathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) MMP pathway inhibitors such as marimastat, ilomastat and metastat, (y) cell motility inhibitors such as cytochalasin B, (z) antiproliferative/antineoplastic agents including antimetabolites such as purine analogs (e.g., 6-mercaptopurine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, paclitaxel and epothilone), caspase activators, proteasome inhibitors, angiogenesis inhibitors (e.g., endostatin, angiostatin and squalamine), rapamycin, cerivastatin, flavopiridol and suramin, (aa) matrix deposition/organization pathway inhibitors such as halofuginone or other quinazolinone derivatives and tranilast, (bb) endothelialization facilitators such as VEGF and RGD peptide, and (cc) blood rheology modulators such as pentoxifylline.

Numerous additional therapeutic agents useful for the practice of the present invention are also disclosed in U.S. Pat. No. 5,733,925 assigned to NeoRx Corporation, the entire disclosure of which is incorporated by reference.

A wide range of therapeutic agent loadings can be used in connection with the medical articles of the present invention, with the therapeutically effective amount being readily determined by those of ordinary skill in the art and ultimately depending, for example, upon the condition to be treated, the age, sex and condition of the patient, the nature of the therapeutic agent, the nature of the ceramic or metallic region(s), the nature of the polyelectrolyte multilayer coating region(s), the nature of the medical article, and so forth.

Once the medical articles of the present invention are contacted with a subject (e.g., a human subject), therapeutic agent is released from the same. The release profile will depend upon a number of factors including: (a) the characteristics of the therapeutic agent(s), including polarity and the molecular size in relation to the ceramic pore size, (b) the manner in which the medical article is contacted with the subject, (c) the type and porosity (if any) of the ceramic or metallic region(s) utilized, and (d) the number and type of the individual polyelectrolyte layers that are selected (as noted above, biodisintegrable polyelectrolyte layers are particularly beneficial, in that one is potentially left with a bare ceramic or metallic skeleton subsequent to biodisintegration).

Although various embodiments of the invention are specifically illustrated and described herein, it will be appreciated that modifications and variations of the present invention are covered by the above teachings without departing from the spirit and intended scope of the invention.

The invention claimed is:

1. A medical article comprising: (a) a ceramic or metallic region whose surface comprises a plurality of depressions; (b) a multilayer coating region comprising multiple polyelectrolyte layers deposited over said surface wherein each polyelectrolyte layer has a net charge opposite in sign from the adjacent layers; and (c) a therapeutic agent disposed within the depressions beneath said multilayer coating region, wherein the multilayer coating region extends over the therapeuticagent-containing surface depressions to provide enclosed cavities which are occupied by the therapeutic agent.

2. The medical article of claim 1, wherein the multilayer coating region extends into the surface depressions of the ceramic or metallic region.

3. The medical article of claim 1, wherein said multilayer coating region is biodisintegrable.

4. The medical article of claim 1, wherein said multilayer coating comprises a polycation layer selected from polyallylamine, polyethyleneimine, poly(dimethyl diallyl ammonium chloride), protamine sulfate, chitosan, gelatin, spermidine, and albumin and a polyanion layer selected from poly(styrene sulfonic acid), poly(aniline sulfonic acid), polyacrylic acid, sodium alginate, polystyrene sulfonate, eudragit, gelatin, hyaluronic acid, carrageenan, chondroitin sulfate, carboxymethylcellulose.

5. The medical article of claim 1, wherein said multilayer coating contains from 2 to 100 polyelectrolyte layers.

6. The medical article of claim 1, wherein said medical article comprises a plurality of multilayer coating regions.

7. The medical article of claim 6, wherein said medical article comprises a first therapeutic agent disposed beneath or within a first multilayer coating region and a second therapeutic agent disposed beneath or within a second multilayer coating region.

8. The medical article of claim 1, wherein said medical article comprises first and second multilayer coating regions that differ from each other with respect to the number or the composition or both the number and composition of the polyelectrolyte layers contained therein.

9. The medical article of claim 1, wherein said ceramic or metallic region is a component of said medical article.

10. The medical article of claim 1, wherein said ceramic or metallic region is disposed as a layer over at least a portion of a medical article substrate.

11. The medical article of claim 1, wherein said medical article comprises a plurality of ceramic or metallic regions.

12. The medical article of claim 1, wherein said therapeutic agent is selected from anti-thrombotic agents, anti-proliferative agents, anti-inflammatory agents, anti-migratory agents, agents affecting extracellular matrix production and organization, antineoplastic agents, anti-mitotic agents, anesthetic agents, anti-coagulants, vascular cell growth promoters, vascular cell growth inhibitors, a cholesterol-lowering agents, vasodilating agents, and agents that interfere with endogenous vasoactive mechanisms.

13. The medical article of claim 1, wherein said medical article comprises a plurality of therapeutic agents.

14. The medical article of claim 1, wherein said medical article is an implantable or insertable medical device.

15. The medical article of claim 14, wherein said implantable or insertable medical device is a stent.

16. The medical article of claim 14, wherein said implantable or insertable medical device is selected from a catheter, a guide wire, a filter, a stent graft, a vascular graft, a vascular patch, a shunt, a vena cava filter, a pacemaker, a pacemaker lead, and an orthopedic implant.

17. The medical article of claim 14, wherein said implantable or insertable medical device is adapted for implantation or insertion into the vasculature.

18. The medical article of claim 14, wherein said implantable or insertable medical device is adapted for implantation or insertion into the esophagus, trachea, colon, biliary tract, ureter, urethra, urinary tract, prostate or brain.

19. The medical article of claim 14, wherein said multilayer coating region is biodisintegrable.

20. The medical article of claim 19, wherein said multilayer coating comprises a polycation layer selected from protamine sulfate, chitosan, gelatin, spermidine, and albumin and a polyanion layer selected from sodium alginate, gelatin, hyaluronic acid, carrageenan, and chondroitin sulfate.

21. The medical article of claim 1, wherein said multilayer coating comprises 3 or more polyelectrolyte layers.

22. A method of making the medical article of claim 21, comprising: depositing a first polyelectrolyte layer having a first net charge over the substrate, depositing a second polyelectrolyte layer having a second net charge that is opposite in sign to the first net charge over the first polyelectrolyte layer, and depositing additional polyelectrolyte layers, each having a net charge that is opposite in sign to the preceding layer.

23. The medical article of claim 1, wherein said depressions are pores having an average pore size ranging from 2-50 nanometers.

24. The medical article of claim 1, wherein said depressions are pores having an average pore size ranging from 50 nanometers to 5 microns.

25. The medical article of claim 1, wherein said substrate has a net surface charge, inherent or applied.

26. The medical article of claim 1, wherein each polyelectrolyte layer comprises a single polyelectrolyte species.

27. A medical article comprising: (a) a ceramic region whose surface comprises a plurality of depressions; (b) a biodisintegrable polyelectrolyte multilayer coating region comprising multiple polyelectrolyte layers deposited over said surface wherein each layer has a net charge opposite in sign from the adjacent layers; and (c) a therapeutic agent disposed beneath or within said multilayer coating region.

28. The medical article of claim 27, wherein said ceramic region is a porous ceramic region.

29. The medical article of claim 28, wherein said medical article comprises a plurality of porous ceramic regions of different composition and porosity.

30. The medical article of claim 28, wherein said porous ceramic region has an average pore size ranging from 0.3 to 100 nm.

31. The medical article of claim 28, wherein said porous ceramic region comprises a ceramic material selected from aluminum oxide, titanium oxide, iridium oxide and calcium phosphate ceramics.

32. The medical article of claim 28, wherein said medical article is a stent.

33. The medical article of claim 1, wherein said medical article comprises a metallic region.

34. The medical article of claim 33, wherein said depressions are laser cut depressions.

35. The medical article of claim 33, wherein said medical article is a stent.

36. A medical article comprising: (a) a metallic region whose surface comprises a plurality of depressions; (b) a biodisintegrable polyelectrolyte multilayer coating region comprising multiple polyelectrolyte layers deposited over said surface, wherein each layer has a net charge opposite in sign from the adjacent layers; and (c) a therapeutic agent disposed beneath or within said multilayer coating region, wherein said depressions are through-holes.

37. A medical article comprising: (a) a ceramic or metallic region whose surface comprises a plurality of depressions; (b) a multilayer coating region comprising multiple polyelectrolyte layers deposited over said surface; and (c) a therapeutic agent disposed beneath or within said multilayer coating region, wherein said multilayer coating further comprises metal or metal oxide nanoparticles.

38. A method of making a medical article that comprises: (a) a ceramic or metallic region whose surface comprises a plurality of depressions; (b) a multilayer coating region comprising 3 or more polyelectrolyte layers deposited over said surface wherein each polyelectrolyte layer has a net charge opposite in sign from the adjacent layers; and (c) a therapeutic agent disposed beneath or within said multilayer coating region, said method comprising (a) inserting a disintegrable material into said depressions to form filled depressions, (b) depositing said polyelectrolyte layers over the filled depressions by a method comprising depositing a first polyelectrolyte layer having a first net charge over the substrate, depositing a second polyelectrolyte layer having a second net charge that is opposite in sign to the first net charge over the first polyelectrolyte layer, and depositing additional polyelectrolyte layers, each having a net charge that is opposite in sign to the preceding layer, (c) subsequently removing the disintegrable material from the depressions and (d) subsequently introducing said therapeutic agent into the depressions.

* * * * *

UNITED STATES PATENT AND TRADEMARK OFFICE
CERTIFICATE OF CORRECTION

PATENT NO. : 7,744,644 B2
APPLICATION NO. : 10/805576
DATED : June 29, 2010
INVENTOR(S) : Weber et al.

It is certified that error appears in the above-identified patent and that said Letters Patent is hereby corrected as shown below:

Col. 3, line 49, after "elimination", insert -- of --.

Col. 3, line 57, after "4", change "6" to -- 8 --.

Col. 5, line 67, after "primary pore size", delete "is".

Col. 9, line 9, before "is", change "$X^{31}$" to -- $X^-$ --.

Col. 13, line 13, after "nonetheless", insert -- be --.

Col. 14, line 9, after "be", change "fill" to -- filled --.

Col. 16, line 38, after "BMP-7 (OP-1),", change "BMP-0," to -- BMP-8, --.

Col. 16, line 38, after "BMP-8,", insert -- BMP-9, BMP-10, --.

Signed and Sealed this

Twenty-eighth Day of September, 2010

David J. Kappos
*Director of the United States Patent and Trademark Office*